United States Patent [19]

Iqbal

[11] Patent Number: 4,474,952
[45] Date of Patent: Oct. 2, 1984

[54] PROCESS FOR THE PREPARATION OF METAL COMPLEXES OF ISOINDOLINAZINES

[75] Inventor: Abul Iqbal, Ettingen, Switzerland

[73] Assignee: Ciba-Geigy Corporation, Ardsley, N.Y.

[21] Appl. No.: 417,748

[22] Filed: Sep. 13, 1982

Related U.S. Application Data

[62] Division of Ser. No. 242,006, Mar. 9, 1981, abandoned.

[30] Foreign Application Priority Data

Mar. 13, 1980 [CH] Switzerland .................... 1977/80

[51] Int. Cl.³ .................... C07F 15/00; C09B 57/04
[52] U.S. Cl. .................... 544/225; 546/7; 548/105; 548/106; 548/403; 106/288 Q
[58] Field of Search .................... 542/417; 544/225; 546/7; 548/105, 106, 403

[56] References Cited

U.S. PATENT DOCUMENTS 3,974,149 8/1976 L'Eplattenier et al. ............ 542/417
4,022,770 5/1977 L'Eplattenier et al. ............ 542/417
4,366,312 12/1982 Iqbal .................... 542/417

*Primary Examiner*—Donald G. Daus
*Assistant Examiner*—Diana G. Rivers
*Attorney, Agent, or Firm*—Luther A. R. Hall

[57] ABSTRACT

Process for the preparation of 1:1 metal complexes of azines of the formula

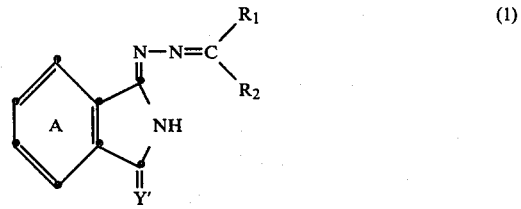

in which $R_1$ is an H atom or an alkyl or aryl group, $R_2$ is an isocyclic or heterocyclic radical with a hydroxyl or mercapto group adjacent to the azomethine group, Y' is the radical of a methylene-active compound or of an aryl- or heteroaryl-amine and the ring A can have substituents which do not confer solubility in water, which comprises heating a hydrazone of the formula

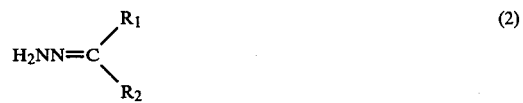

with an isoindolinone of the formula

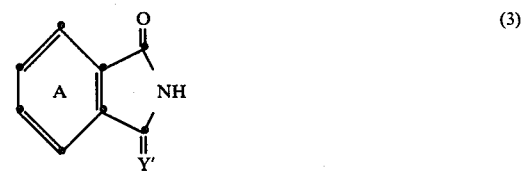

in which $R_1$, $R_2$, A and Y' are as defined, in the presence of a metal donor, in a polar organic solvent.

8 Claims, No Drawings

PROCESS FOR THE PREPARATION OF METAL COMPLEXES OF ISOINDOLINAZINES

This is a divisional of application Ser. No. 242,006, filed on Mar. 9, 1981, now abandoned.

British Patent Specification No. 1,467,595 describes the preparation of 1:1 metal complexes of azines of the formula

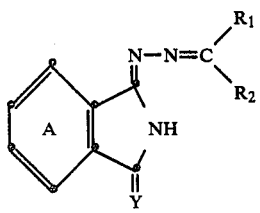
(1)

in which $R_1$ is an H atom or an alkyl or aryl group, $R_2$ is an isocyclic or heterocyclic radical with a hydroxyl group adjacent to the azomethine group, Y is the radical of a methylene-active compound or of an aryl- or heteroaryl-amine and the ring A can have substituents which do not confer solubility in water, by condensing a hydrazone of the formula

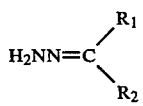
(2)

with an isoindoline of the formula

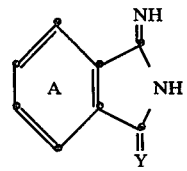
(3)

and treating the compounds of the formula (1) with metal donors. Although this gives the compound of the formula (1) in good yield, the 1:1 nickel complexes obtained therefrom give colourations of unsatisfactory purity and inadequate fastness properties in plastics and surface coatings. The condensation of the isoindoline of the formula (3) with the hydrazone of the formula (2), in the presence of metal salts, likewise leads to unsatisfactory results.

It has now been found that the 1:1 metal complexes of the azines of the formula

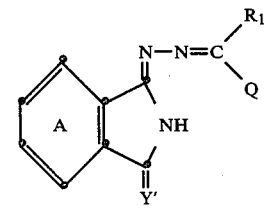
(4)

in which A and $R_1$ are as defined, Q is an isocyclic or heterocyclic radical with a hydroxyl or mercapto group adjacent to the azomethine group and Y' is the radical of a methylene-active compound or of an aryl- or heteroaryl-amine, are obtained in especially high purity by heating a hydrazone of the formula

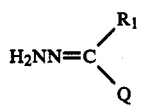
(5)

with an isoindolinone of the formula

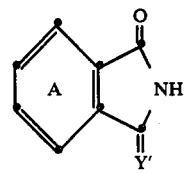
(6)

in the presence of a metal donor, in a polar organic solvent.

The novel 1:1 metal complexes of azines of the formula

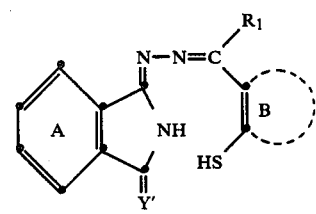
(7)

in which A, $R_1$ and Y' are as defined above and B is an isocyclic or heterocyclic radical, which complexes are obtainable by the process according to the invention, are a further subject of the invention. $R_1$ is, for example, an H atom or preferably a methyl group. B is a phenyl or naphthalene radical or a 5- or 6-membered heterocyclic ring which has an O, S or especially N atom in the $\alpha$- or $\gamma$-position to the C atom on which the mercapto group is located, and which, if desired, also contains a further N atom in the ring and, if desired, contains a fused benzene ring and/or a further heterocyclic ring.

B is preferably a heterocyclic radical, for example of the pyrimidine, quinoline or preferably pyrazole series, and in particular a heterocyclic radical of the formula

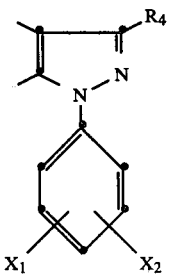
(8)

in which $R_4$ is an alkyl group having 1–4 C atoms, an alkoxycarbonyl group having 2–6 C or a carbamoyl group, $X_1$ is an H, chlorine or bromine atom, a nitro, trifluoromethyl, carbamoyl or sulfamoyl group, an alkyl, alkoxy or alkylsulfamoyl group having 1–4 C, an alkanoylamino, alkylcarbamoyl or alkoxycarbonyl group having 2–6 C, or a phenoxy, benzoylamino, phenylcarbamoyl, phenylsulfamoyl or phenylazo group which is unsubstituted or substituted by chlorine or bromine atoms or methyl groups, and $X_2$ is an H, chlorine or bromine atom or an alkyl or alkoxy group having 1–4 C. The formulae (1) and (7) in each case represent one of the possible isomeric forms.

The hydrazones of the formula (5) are obtained by the known process of reacting an oxo compound of the formula

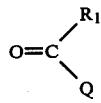   (9)

in which $R_1$ and Q are as defined, or its aldimine with hydrazine hydrate. Of particular value are aldehydes or ketones of the formula

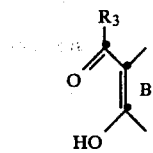   (10)

in which $R_3$ is an H atom or preferably a methyl group and B is a phenyl or naphthalene radical or a 5- or 6-membered heterocyclic ring which has an O, S or especially N atom in the α- or γ-position to the C atom on which the hydroxyl group is located, and, if desired, also contains a further N atom in the ring and, if desired, contains a fused benzene ring and/or a further heterocyclic ring.

B is preferably a radical of the pyrazole, pyridine, pyrimidine, quinoline or coumarin series.

Oxo compounds of the formula

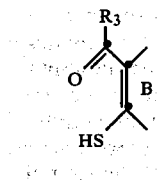   (11)

are preferred.

Examples of oxo compounds are the aldehydes and ketones listed in British Pat. No. 1,467,595 and also 1-phenyl-3-methyl-4-formyl-5-mercapto-pyrazole, 1-o-, m- or p-chlorophenyl-3-methyl-4-formyl-5-mercapto-pyrazole, 1-o-, m- or p-methylphenyl-3-methyl-4-formyl-5-mercapto-pyrazole, 1-phenyl-3-methyl-4-acetyl-5-mercapto-pyrazole, 1-o-, m- or p-chlorophenyl-3-methyl-4-acetyl-5-mercapto-pyrazole, 1-o-, m- or p-methylphenyl-3-methyl-4-acetyl-5-mercapto-pyrazole, 2-formyl-5,5-dimethyl-cyclohexyl-1,3-dione, 2-mercapto-benzaldehyde, 2-mercapto-acetophenone, 3-acetyl-2,4-dimercapto-quinoline, 3-formyl-2,4-dimercapto-quinoline, 3-formyl-2-mercapto-quinoline, 3-formyl-2,4,6-trimercapto-pyrimidine, 3-acetyl-2,4,6-trimercapto-pyrimidine, 4-mercaptocoumarin and 2-formyl-1,3-dithiono-5,5-dimethylcyclohexane.

The isoindolinones of the formula (6) are obtained by the known process of condensing an isoindolinone of the formula

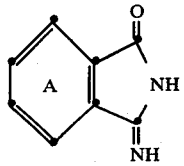   (12)

a phthalodinitrile or an o-cyanobenzoic acid ester with a methylene-active compound or an aryl- or heteroarylamine. Methylene-active compounds are, in particular, those of the formula

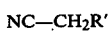

NC—CH$_2$R' in which R' is a cyano group, an alkoxycarbonyl, alkylcarbamoyl or alkanoyl group having 2–6 C, a benzoyl, carbamoyl or sulfamoyl group, a benzylcarbamoyl group or a phenylsulfamoyl or phenylsulfonyl group which is unsubstituted or substituted by halogen atoms or alkyl groups having 1–4 C, but especially a group of the formula

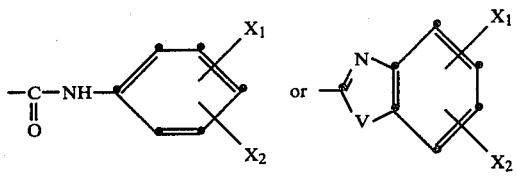

in which $X_1$ and $X_2$ are defined and V is O, S or NH.

Examples are the acetonitriles listed on page 7 of British Patent Specification No. 1,467,595 and also cyanoacetic acid o-chlorophenylamide, p-chlorophenylamide, m-chlorophenylamide, m-methylphenylamide, p-methylphenylamide, 3,4-dichlorophenylamide, 3,5-dimethylphenylamide, 3,4-dimethylphenylamide, 3-chloro-4-methylphenylamide, o-methoxyphenylamide, 2,4-dimethoxyphenylamide, 2,5-dimethoxyphenylamide, p-acetylamino-phenylamide, p-benzoylamino-phenylamide, 3-chloro-4-p-chlorobenzoylamino-phenylamide, 4-carbamoylphenylamide, 4-sulfamoyl-phenylamide, 4-phenylazophenylamide, 4-phenoxyphenylamide, p-nitrophenylamide, 3-trifluoromethyl-phenylamide or 2-chloro-5-trifluoromethyl-phenylamide, and 2-cyanomethyl-4-phenyl-, -4-p-nitrophenyl, -4-fluorophenyl- or -4-methylphenylthiazole.

Further possible methylene-active compounds are heterocyclic compounds containing one active methylene group in the heterocyclic ring, for example those mentioned on pages 7 and 8 of British Patent Specification No. 1,467,595, for example 2,4-dihydroxyquinoline, 1-p-chlorophenyl-3-methyl-5-pyrazolone, 1-p-methylphenyl-3-methyl-5-pyrazolone, 1-phenyl-3-dichlorovinyl-5-pyrazolone and 1-p-methylphenyl-3-dichlorovinyl-5-pyrazolone.

Examples of amines which donate the radical Y' are aromatic, but especially heterocyclic, amines, preferably those in which the amino group is located directly on a 5-6-membered heterocyclic ring which can contain 1–3 N atoms and also O and S atoms. A substituted or unsubstituted benzene nucleus can be fused to the heterocyclic parent nucleus. Examples are the amines listed on pages 6–7 of British Patent Specification No. 1,467,595, and also 2-aminopyridine, 2-amino-5-chloropyridine, diaminophthalazine, 2-amino-4-hydroxyquinoline, 2,6-diaminopyridine and 2-amino-4,5-dimethylthiazole.

The isoindolinones of the formula (12) are known. They are more readily accessible than corresponding diiminoisoindolines, and this represents a further advantage of the novel process of preparation.

The metal donors used are preferably salts of zinc, cadmium, manganese, cobalt and iron, but especially of copper and nickel, or of mixtures of these metals. The formates, acetates or stearates of these metals are advantageously used.

The reactions take place in a polar solvent, in particular one of a hydrophilic nature, for example an amide, such as dimethylformamide, formamide, dimethylacetamide or N-methylpyrrolidone, or also dimethyl sulfoxide, acetonitrile or an alcohol, for example ethylcellosolve. It is also possible to use a mixture of polar solvents.

The reaction temperature is advantageously between 100° and 200° C.

The metal complex obtained is isolated in the customary manner by filtration. The material on the filter is washed thoroughly with solvent. The pigment is obtained in excellent yield and purity and can be used without further purification, in finely divided form, for colouring high-molecular organic material, for example cellulose ethers and esters, such as ethylcellulose, acetylcellulose and nitrocellulose, polyamides, polyurethanes or polyesters, and natural resins or synthetic resins, for example aminoplasts, in particular urea/formaldehyde and melamine/formaldehyde resins, alkyd resins, phenoplasts, polycarbonates, polyolefins, such as polystyrene, polyvinyl chloride, polyethylene, polypropylene, polyacrylonitrile and polyacrylic acid esters, thermoplastic or curable acrylic resins, rubber, casein, silicone and silicone resins, individually or in mixtures. The high-molecular compounds mentioned can be in the form of plastic masses or melts or in the form of spinning solutions, surface coatings or printing inks. Depending on the intended use, it proves advantageous to use the pigments as toners or in the form of preparations.

The pigment can be employed in the form in which it is obtained in the synthesis, or in a lightly ground form, in which case it produces opaque final colourations. However, it can also be subjected to intensive grinding, in which case transparent final colourations, for example intensely coloured metallic-effect coatings, are obtained.

Pastes of the pigments in surface coatings are distinguished by favourable flow properties.

The colourations obtained, for example in plastics, fibres and surface coatings, are distinguished by high colour intensity, high purity of colour shade, good dispersibility and good fastness to overcoating, migration, heat, light and weather, and also by a good gloss.

In addition to the purity of the end product obtained, further advantages of the process according to the invention are that products substituted in the benzene ring A, and those in which Y' is the radical of a particularly active methylene group, can also be prepared easily.

The success of the process according to the invention is surprising because, hitherto, only reactions of the carbonyl group of isoindolines were known, in which the keto group is first converted to a reactive derivative, for example an imide-chloride or iminoether. Therefore, it could not be expected that isoindolinones of the formula (4) would be capable of reacting directly in a template reaction with hydrazones.

In the following examples, percentages are by weight and degrees are degrees centigrade.

EXAMPLE 1

6.5 g (0.03 mol) of 2,4-dihydroxyquinoline-3-acetylhydrazone and 7.8 g of nickel acetate.4 $H_2O$ (0.315 mol) are dissolved in 150 ml of N-methylpyrrolidone and the solution is warmed to 60° C. 9.7 g of 1-cyano-N-p-chlorophenylcarbamoylmethylene)-isoindolin-3-one are then added. The suspension is warmed to 150° C. and stirred for 1 hour at 150°-155° C. It is filtered hot (80° C.) and the residue is washed with N-methylpyrrolidone and ethanol. After drying at 80° C. in vacuo, 11.34 g (65.3% of theory) of a red metal complex of the composition $C_{28}H_{17}ClN_6O_3Ni$ and of the formula

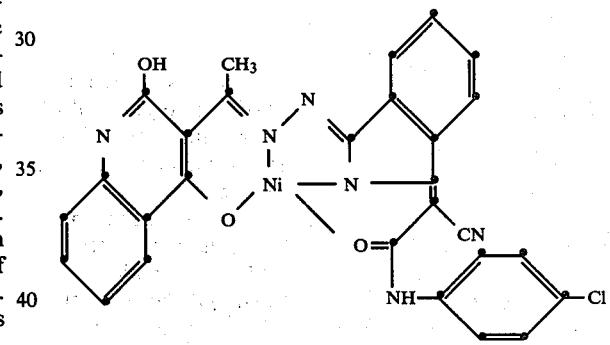

are obtained.

Microanalysis: $C_{28}H_{17}ClN_6O_3Ni$ (MW 579.65): % calculated C 58.02; H 2.96; N 14.50; Cl 6.12; Ni 10.13; % found C 58.1 H 3.2 N 14.7 Cl 5.7 Ni 9.95

EXAMPLE 2

1.32 g (0.007 mol) of dichlorosalicylaldehyde-hydrazone and 1.83 g (0.00735 mol) of nickel acetate. $4H_2O$ are suspended in 60 ml of N-methylpyrrolidone and the suspension is warmed to 60° C. 2.00 g (0.007 mol) of 1-(cyano-2-benzimidazolyl-methylene)-3-isoindolinone are added and the mixture is heated to 150° C. After stirring for 2 hours at 150°-155° C., the reaction mixture is cooled to 35° C. and filtered. The residue is washed successively with N-methylpyrrolidone and ethanol and dried overnight in vacuo at 80° C. 1.4 g (36.5% of theory) of the nickel complex of the formula

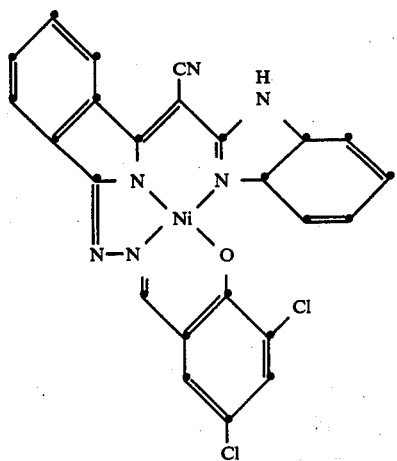

are obtained.

Microanalysis: $C_{24}H_{11}N_6OCl_2Ni$: calculated C 54.49%; H 2.10%; N 15.89%; Cl 13.4% Ni; 11.10%; found C 54.6%; H 2.3%; N 16.1%; Cl 13.6% Ni; 11.4%

The above metal complex colours plastics and surface coatings in red, covering shades with excellent fastness properties.

EXAMPLE 3

1.3 g (0.006 mol) of 2,4-dihydroxy-3-acetylquinoline-hydrazone and 1.57 g (0.0063 mol) of nickel acetate. 4H$_2$O are heated to 60° C. in 50 ml of N-methylpyrrolidone, with stirring. 1.92 g (0.006 mol) of 1-(5'-acetylamino-2'-benzoxazolyl-imino)-3-isoindolinone, prepared from 1-imino-3-oxo-isoindoline and 5-acetylamino-2-amino-benzoxazole, are then added and the mixture is warmed to 140° C. After the reaction mixture has been left to react for 2.5 hours at 140°–45° C., it is cooled to 80° C. and filtered and the reaction product is washed N-methylpyrrolidone and spirit. After drying at 80° C. in vacuo, 3.06 g (88.5% of theory) of an orange metal complex of the composition $C_{28}H_{19}N_7O_4Ni$ and of the formula

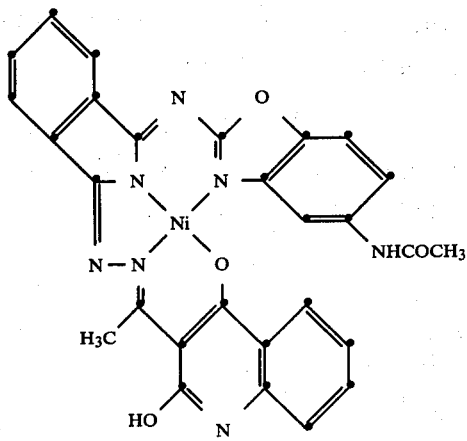

are obtained.

Microanalysis: $C_{28}H_{19}N_7O_4Ni$ MW 576: calculated C 58.36%; H 3.32%; N 17.02%; Ni 10.19%; found C 58.2%; H 3.5%; N 17.2%; Ni 10.0%

The above pigment colours plastics and surface coatings in yellowish orange shades with excellent fastness properties.

EXAMPLE 4

1.75 g (0.008 mol) of 4-hydroxy-3-acetylcoumarin-hydrazone and 2.1 g (0.0084 mol) of nickel acetate are suspended in 60 ml of N-methylpyrrolidone and the suspension is then warmed to 60° C. The resulting suspension is treated with 2.32 g (0.008 mol) of 1-(2',4'-dioxo-quinolin-3'-ylidene)-3-isoindolinone, prepared from 1-imino-3-oxoisoindoline and 2,4-dihydroxyquinoline, and heated to 140°. The mixture is left to react for 2 hours at 140°–45° C. and the metal complex which has precipitated out is then filtered off from the mother liquor. After washing with N-methylpyrrolidone and spirit and drying in vacuo at 80° C., 3.0 g (68.5% of theory) of a red metal complex pigment of the formula

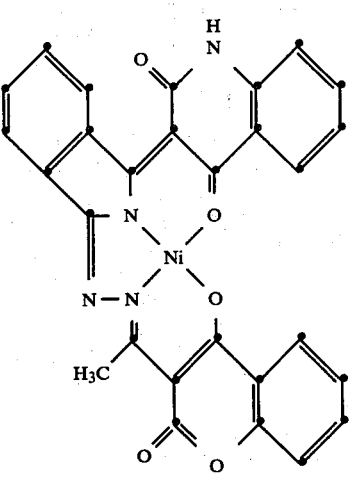

are obtained. The above metal complex colours plastics and surface coatings in pure red shades with excellent fastness properties.

Microanalysis: $C_{27}H_{14}N_4O_5Ni$: MW 533 calculated C 60.83%; H 2.65%; N 10.51%; Ni 11.01%; found C 60.9%; H 2.4%; N 10.8%; Ni 10.9%

EXAMPLE 5

1.68 g (0.006 mol) of 2,4-dihydroxy-3-benzoylquinoline-hydrazone and 1.57 g (0.0063 mol) of nickel acetate 4H$_2$O are suspended in 50 ml of N-methylpyrrolidone and the suspension is warmed to 60° C. 1.95 g (0.006 mol) of 1-(cyano-N-p-chlorophenylcarbamoyl-methylene)-isoindolin-3-one are then added. The suspension is warmed to 145° C. and stirred for 1½ hours at 145°–150° C. It is filtered hot (80° C.) and the residue is washed with N-methylpyrrolidone and ethanol. After drying at 80° C. in vacuo, 2.34 g (61% of theory) of a red metal complex of the formula

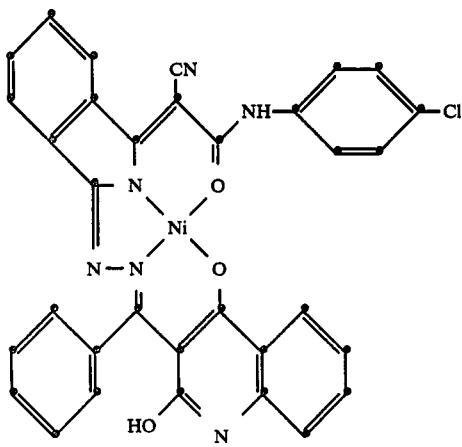

are obtained.

Microanalysis: $C_{33}H_{19}ClN_6O_3Ni$ (sic): MW 642 calculated C 61.77%; H 2.98%; N 13.1%; CL 5.53%; Ni 9.15%; found C 61.2%; H 3.00%; N 13.1%; Cl 5.4%; Ni 9.42%

The above metal complex pigment colours plastics and surface coatings in the pure red shades with excellent fastness properties.

EXAMPLE 6

1.95 g (0.008 mol) of 2-anilinomethylene-1,3-dioxo-5,5-dimethyl-cyclohexane, prepared from aniline, orthoformic acid ester and 1,3-dioxo-5,5-dimethyl-cyclohexane, are dissolved in 50 ml of dimethylformamide. After 0.4 ml (0.008 mol) of hydrazine hydrate has been added, the mixture is stirred at room temperature for 1 hour. 2.1 g (0.0084 mol) of nickel acetate. $4H_2O$ are then added and the mixture is warmed to 60° C. It is then treated with 2.29 g (0.008 mol) of 1-(cyanobenzimidazolyl-methylene)-3-isoindolinone and heated to 135° C. After 2½ hours, the reaction mixture is cooled to 80° C. and the metal complex which has precipitated out is filtered off. After washing with dimethylformamide and spirit and drying at 80° C. in vacuo, 3.5 g (86.3% of theory) of an orange compound of the formula

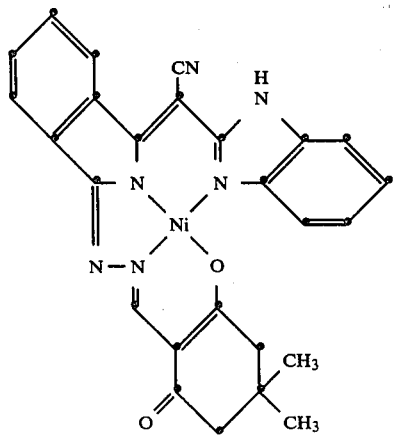

are obtained.

Microanalysis: $C_{26}H_{20}N_6O_2Ni$: MW 507.2 calculated C 61.57%; H 3.97%; N 16.57%; Ni 11.58%; found C 61.4%; H 4.1%; N 16.8%; Ni 11.6%

The above complex colours plastics and surface coatings in the pure yellowish orange shades with excellent fastness properties.

EXAMPLE 7

1.95 g (0.008 mol) of 2-anilinomethylene-1,3-dioxo-5,5-dimethyl-cyclohexane are dissolved in 50 ml of N-methylpyrrolidone and treated with 0.4 ml (0.008 mol) of hydrazine hydrate and the mixture is stirred at room temperature for 1 hour. 2.1 g (0.0084 mol) of nickel acetate. $4H_2O$ are added and the mixture is warmed to 60° C. 3.2 g (0.008 mol) of 1-benzimidazolylimino-4,5,6,7-tetrachloro-3-oxo-isoindoline are then introduced and the mixture is warmed to 145° C. It is stirred for 1 hour at the same temperature and then cooled (to 80° C.). The metal complex which has precipitated out is filtered off, washed with N-methylpyrrolidone and ethanol and dried overnight at 80° C. in vacuo. 3.9 g (78.5% of theory) of a red pigment of the formula,

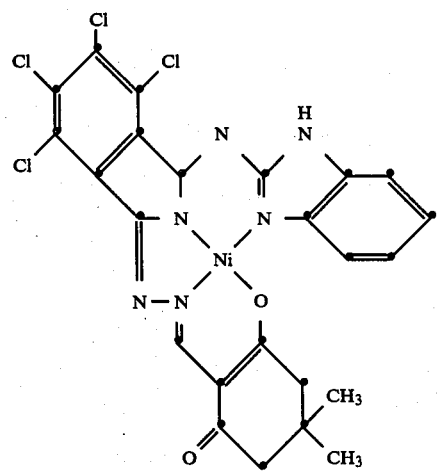

are obtained, which colours plastics and surface coatings in red shades with excellent fastness properties.

Microanalysis: $C_{24}H_{16}Cl_4N_6O_2Ni$: MW 621 calculated C 46.42%; H 2.60%; N 13.53%; Cl 22.84%; Ni 9.45%; found C 46.7%; H 2.7%; N 13.8%; Cl 22.3%; Ni 9.36%

EXAMPLE 8

2.35 g (0.008 mol) of 1-phenyl-3-methyl-4-anilinomethylene-5-mercaptopyrazole are dissolved in 50 ml of dimethylformamide. After 0.4 ml (0.008 mol) of hydrazine hydrate has been added, the mixture is stirred at room temperature for 1 hour and then treated with 2.1 g (0.0084 mol) of nickel acetate. $4H_2O$ and warmed to 60° C. 2.22 g (0.008 mol) of 1-(cyano-benzimidazolyl-methylene)-3-oxo-isoindoline are then introduced and the mixture is heated to 130° C. After a reaction time of 2 hours at 130°–135° C., the mixture is cooled to 80° C. and filtered. The filtration residue is washed with dimethylformamide and ethanol and dried overnight at 80° C. in vacuo. 2.8 g (63% of theory) of a red metal complex of the formula

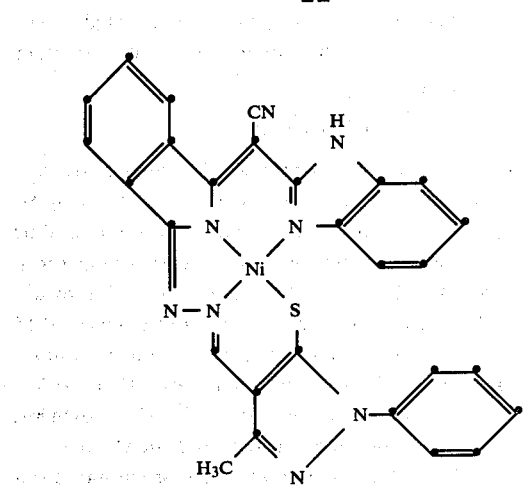

are obtained.

Microanalysis: $C_{28}H_{18}N_8SNi$: MW 557 calculated C 60.35%; H 3.26%; N 20.11%; S 5.75%; Ni 10.54%; found C 60.3%; H 3.4%; N 20.0%; S 5.2%; Ni 10.3%

EXAMPLE 9-76

Analogously to Examples 1-8, further 1:1 nickel complexes are obtained by condensing the hydrazone of the oxo compounds indicated in column 2 of Table 1 with the isoindolinone of the formula

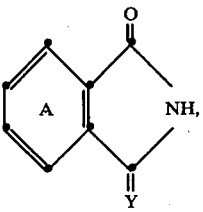

the latter having been obtained by condensing the 3-iminoisoinidolinone mentioned in column 3 with the compounds $YH_2$ listed in column 4. Column 5 gives the shade in PVC.

TABLE 1

| Example No. | Oxo compound | Isoindolinone | $YH_2$ | Shade in PVC |
|---|---|---|---|---|
| 9 | 1-p-Tolyl-3-methyl-4-acetyl-pyrazol-5-one | 3-Imino-isoindolinone | Cyanoacet-anilide | red |
| 10 | 1-p-Chlorophenyl-3-methyl 4-formyl-pyrazol-5-one | 3-Imino-isoindolinone | Cyanoacetic acid p-chloroanilide | scarlet |
| 11 | 3-Acetyl-2,4-dihydroxy-quinoline | 3-Imino-isoindolinone | Ethyl cyanoacetate | red |
| 12 | 3-Acetyl-2,4-dihydroxy-quinoline | 3-Imino-isoindolinone | Cyanoacetic acid ethylamide | red |
| 13 | 3-Acetyl-2,4-dihydroxy-quinoline | 3-Imino-isoindolinone | Acetoacetonitrile | red |
| 14 | 3-Acetyl-2,4-dihydroxy-quinoline | 3-Imino-isoindolinone | Cyanoacetic acid p-methoxyanilide | red |
| 15 | 3-Acetyl-2,4-dihydroxy-quinoline | 3-Imino-isoindolinone | Cyanoacetic acid benzylamide | red |
| 16 | 3-Acetyl-2,4-dihydroxy-quinoline | 3-Imino-isoindolinone | Benzoylacetonitrile | red |
| 17 | 3-Acetyl-2,4-dihydroxy-quinoline | 3-Imino-isoindolinone | Cyanomethane-p-tolyl-sulfonamide | red |
| 18 | 3-Acetyl-2,4-dihydroxy-quinoline | 3-Imino-isoindolinone | Cyanomethane-p-chlorophenyl-sulfonamide | red |
| 19 | 3-Acetyl-2,4-dihydroxy-quinoline | 3-Imino-isoindolinone | Cyanoacetic acid p-sulfamoylanilide | red |
| 20 | 3-Acetyl-2,4-dihydroxy-quinoline | 3-Imino-isoindolinone | Cyanoacetic acid p-carbamoylanilide | red |
| 21 | 3-Acetyl-2,4-dihydroxy-quinoline | 3-Imino-isoindolinone | Phenylsulfonylacetonitrile | red |
| 22 | 3-Acetyl-2,4-dihydroxy-quinoline | 3-Imino-iso-indolinone | Cyanoacetic acid p-benzoylaminoanilide | red |
| 23 | 3-Acetyl-2,4- | 3-Imino-iso- | Cyanoacetic | red |

TABLE 1-continued

| Example No. | Oxo compound | Isoindolinone | YH$_2$ | Shade in PVC |
|---|---|---|---|---|
| | dihydroxy-quinoline | indolinone | acid p-acetylamino-anilide | |
| 24 | 3-Acetyl-2,4-dihydroxy-quinoline | 3-Imino-4,5,6,7-tetrachloro-isoindolin-1-one | Cyanoacetic acid p-chloro-anilide | orange |
| 25 | 3-Acetyl-2,4-dihydroxy-quinoline | 3-Imino-,-dimethoxy-,-dichloro-iso-indolinone | Cyanoacetic acid p-chloro-anilide | orange |
| 26 | 3-Acetyl-2,4-dihydroxy-quinoline | 3-Imino-4,5,6,7-tetrachloro-isoindolinone | 2-Cyano-methyl-benzimidazole | violet |
| 27 | 3-Acetyl-2,4-dihydroxy-quinoline | 3-Imino-iso-indolinone | Cyanoacetic acid m-chloro-anilide | red |
| 28 | 3-Acetyl-2,4-dihydroxy-quinoline | 3-Imino-iso-indolinone | Cyanoacetic acid 3',4'-dichloro-anilide | scarlet |
| 29 | 3-Acetyl-2,4-dihydroxy-quinoline | 3-Imino-iso-indolinone | 2-Cyano-methylbenzimidazole | red |
| 30 | 3-Acetyl-2,4-dihydroxy-quinoline | 3-Imino-iso-indolinone | 2-Cyano-methyl-benzothiazole | red |
| 31 | 3-Acetyl-2,4-dihydroxy-quinoline | 3-Imino-iso-indolinone | 2-Cyano-methyl-benzoxazole | scarlet |
| 32 | 3-Acetyl-2,4-dihydroxy-quinoline | 3-Imino-iso-indolinone | Cyanoacetanilide | red |
| 33 | 1-p-Chlorophenyl-3-methyl-4-acetyl-pyrazol-5-one | 3-Imino-iso-indolinone | Cyanoacetic acid p-acetylaminoanilide | red |
| 34 | 3-Acetyl-2,4-dihydroxy-quinoline | 3-Imino-iso-indolinone | Cyanoacetic acid p-nitro-anilide | red |
| 35 | 3-Acetyl-2,4-dihydroxy-quinoline | 3-Imino-iso-indolinone | Cyanoacetic acid p-phenyl-azoanilide | red |
| 36 | 3-Acetyl-2,4-dihydroxy-quinoline | 3-Imino-iso-indolinone | Cyanoacetic acid m-trifluoromethyl-anilide | scarlet |
| 37 | 3-Acetyl-2,4-dihydroxy-quinoline | 3-Imino-iso-indolinone | Cyanoacetic acid p-phenoxyanilide | red |
| 38 | 3-Acetyl-2,4-dihydroxy-quinoline | 3-Imino-iso-indolinone | Cyanoacetic acid 3'-chloro-4'-methylanilide | red |
| 39 | 3-Acetyl-2,4-dihydroxy-quinoline | 3-Imino-iso-indolinone | Cyanoacetic acid acetylaminoanilide | red |
| 40 | 3-Acetyl-2,4-dihydroxy-quinoline | 3-Imino-iso-indolinone | Cyanoacetic acid p-phenyl-sulfamoyl-anilide | red |
| 41 | 3-Acetyl-2,4-dihydroxy-quinoline | 3-Imino-iso-indolinone | Cyanoacetic acid p-phenyl-carbamoyl-anilide | red |
| 42 | 3-Acetyl-2,4-dihydroxy-quinoline | 3-Imino-iso-indolinone | Cyanoacetic acid o-ethoxycarbonyl-anilide | red |
| 43 | 3-Acetyl-2,4-dihydroxy-quinoline | 3-Imino-iso-indolinone | 2-Cyano-methyl-4-p-fluoro-phenyl-thiazole | red |
| 44 | 3-Acetyl-2,4-dihydroxy-quinoline | 3-Imino-5,6-dichloro-iso-indolinone | Barbituric acid | orange |

TABLE 1-continued

| Example No. | Oxo compound | Isoindolinone | YH₂ | Shade in PVC |
|---|---|---|---|---|
| 45 | 3-Acetyl-2,4-dihydroxy-quinoline | 3-Imino-iso-indolinone | 1-p-Tolyl-3-β,β-dichloro-vinyl-pyrazol-5-one | Bordeaux red |
| 46 | 3-Acetyl-2,4-dihydroxy-quinoline | 3-Imino-iso-indolinone | Barbituric acid | red |
| 47 | 3-Acetyl-2,4-dihydroxy-quinoline | 3-Imino-iso-indolinone | 1-Phenyl-3-methyl-pyrazol-5-one | red |
| 48 | 3-Acetyl-2,4-dihydroxy-quinoline | 3-Imino-4,5,6,7-tetra-chloro-iso-indolinone | Barbituric acid | orange |
| 49 | 3-Acetyl-2,4-dihydroxy-quinoline | 3-Imino-4,5,6,7-tetra-chloro-iso-indolinone | 2-Cyanomethyl-benzimidazole | violet |
| 50 | 3-Acetyl-2,4-dihydroxy-quinoline | 3-Imino-4,5,6,7-tetra-chloro-iso-indolinone | Cyanoacetic acid 2',-5'-dimethoxy-anilide | red |
| 51 | 3-Acetyl-2,4-dihydroxy-quinoline | 3-Imino-4,5,6,7-tetra-chloro-iso-indolinone | Cyanoacetic acid 3',4'-dimethyl-anilide | red |
| 52 | 2,4,6-Trihydroxy-5-acetylpyrimidine | 3-Imino-4,5,6,7-tetra-chloro-iso-indolinone | 2-Aminoimidazole | orange |
| 53 | 3-Acetyl-2,4-dihydroxy-quinoline | 3-Imino-4,5,6,7-tetra-chloro-iso-indolinone | (benzofuro-benzimidazol-2-amine structure) | orange |
| 54 | 3-Acetyl-2,4-dihydroxy-quinoline | 3-Imino-4,5,6,7-tetra-chloro-iso-indolinone | 2-Amino-5-methyl-benzoylamino-benzimidazole | orange |
| 55 | 3-Acetyl-2,4-dihydroxy-quinoline | 3-Imino-4,5,6,7-tetra-chloro-iso-indolinone | 2-Amino-5-p-chloro-benzoylamino-benzimidazole | orange |
| 56 | 3-Acetyl-2,4-dihydroxy-quinoline | 3-Imino-4,5,6,7-tetra-chloro-iso-indolinone | 2-Amino-5-benzoylamino-benzimidazole | scarlet |
| 57 | 3-Acetyl-2,4-dihydroxy-quinoline | 3-Imino-5,6-dichloro-iso-indolinone | 2-Amino-benz-thiazole | orange |
| 58 | 3-Acetyl-2,4-dihydroxy-quinoline | 3-Imino-iso-indolinone | 2-Aminothiazole | orange |
| 59 | 3-Acetyl-2,4-dihydroxy-quinoline | 3-Imino-5,6-dichloro-iso-indolinone | 2-Amino-5-ethoxy-benz-imidazolone | red |
| 60 | 3-Acetyl-2,4-dihydroxy-quinoline | 3-Imino-4,5,6,7-tetra-chloro-iso-indolinone | 2-Amino-benz-thiazole | red |
| 61 | 3-Acetyl-2,4-dihydroxy-quinoline | 3-Imino-4,5,6,7-tetra-chloro-iso-indolinone | 2-Amino-benz-imidazole | red |
| 62 | 3-Acetyl-4-hydroxy-coumarin | 3-Imino-4,5,6,7-tetra-chloro-iso-indolinone | 2-Amino-benz-imidazole | orange |
| 63 | 3-Acetyl-2,4-dihydroxy-quinoline | 3-Imino-iso-indolinone | 2-Amino-benz-imidazole | orange |
| 64 | 3-Acetyl-2,4-dihydroxy-quinoline | 3-Imino-iso-indolinone | 2-Amino-benz-imidazole | orange |
| 65 | 3-Acetyl-2,4-dihydroxy-quinoline | 3-Imino-iso-indolinone | 1,4-Diamino-phthalazine | scarlet |

TABLE 1-continued

| Example No. | Oxo compound | Isoindolinone | YH₂ | Shade in PVC |
|---|---|---|---|---|
| | quinoline | | | |
| 66 | 1-Phenyl-3-methyl-4-formyl-5-mercapto-pyrazole | 3-Imino-iso-indolinone | Cyanoacet-anilide | red |
| 67 | 1-Phenyl-3-methyl-4-formyl-5-mercapto-pyrazole | 3-Imino-iso-indolinone | Cyanoacetic acid 4'-phenoxyanilide | red |
| 68 | 1-Phenyl-3-methyl-4-formyl-5-mercapto-pyrazole | 3-Imino-iso-indolinone | Cyanoacetic acid 4'-acetylamino-anilide | red |
| 69 | 1-Phenyl-3-methyl-4-formyl-5-mercapto-pyrazole | 3-Imino-iso-indolinone | Cyanoacetic acid 4'-methyl-anilide | red |
| 70 | 1-Phenyl-3-methyl-4-formyl-5-mercapto-pyrazole | 3-Imino-iso-indolinone | Cyanoacetic acid 4'-methoxyanilide | red |
| 71 | 1-Phenyl-3-methyl-4-formyl-5-mercapto-pyrazole | 3-Imino-iso-indolinone | Cyanoacetic acid 4'-chloroanilide | red |
| 72 | 1-p-Chlorophenyl-3-methyl-4-acetylpyrazol-5-one | 3-Imino-4,6-dimethoxy-5,7-dichloro-isoindolinone | Cyanoacet-amide | Bordeaux red |
| 73 | 1-p-Chlorophenyl-3-methyl-4-acetylpyrazol-5-one | 3-Imino-5,6-dichloro-iso-indolinone | Cyanoacet-amide | red |
| 74 | 1-p-Chlorophenyl-3-methyl-4-acetylpyrazol-5-one | 3-Imino-4,6-dimethoxy-5,7-dichloro-isoindolinone | Cyanoacet-amide | Bordeaux red |
| 75 | 3-Acetyl-4-hydroxy-coumarin | 3-Imino-4,6-dimethoxy-5,7-dichloro-isoindolinone | Cyanoacet-amide | red |
| 76 | 3-Acetyl-4-hydroxy-coumarin | 3-Imino-5,6-dichloro-iso-indolinone | Cyanoacet-amide | red |
| 77 | 1-Phenyl-3-alkoxycarbonyl-4-formyl-5-mercaptopyrazole | 3-Imino-iso-indolinone | Cyanomethyl-benzimidazole | red |
| 78 | 1-Phenyl-3-thio-carbamoyl-4-formyl-5-mercaptopyrazole | 3-Imino-iso-indolinone | 2-Aminobenz-imidazole | orange |
| 79 | 7-Chloro-4-methoxy-3-formyl-2-mercapto-quinoline | 3-Imino-iso-indolinone | Cyanoacetic acid p-chloro-anilide | red |

EXAMPLES 80–82

By reacting the isoindolinone derivative of the formula

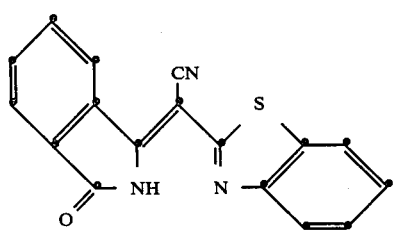

with the hydrazone of the formula

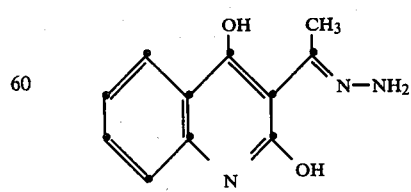

in the presence of the acetate of the metal listed in column 2 of Table 2, analogously to Examples 1–8, further metal complexes of the formula

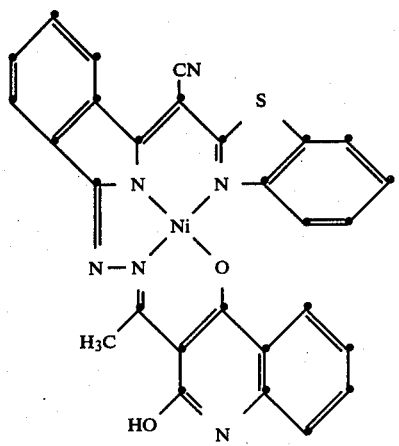

are obtained (for reasons of simplicity, only one of the possible isomeric or tautomeric forms is considered), M being the metal indicated in column 2. Column 3 gives against the shade of the colouration in polyvinyl chloride.

TABLE 2

| Example No. | M | Shade in PVC |
| --- | --- | --- |
| 80 | Pd | red |
| 81 | Cu | red |
| 82 | Zn | scarlet-red |

EXAMPLE 83

25 parts of the pigment prepared according to Example 1, 100 parts of finely ground sodium chloride and 30 parts of diacetone-alcohol are initially introduced into a laboratory kneader with a capacity of 250 parts by volume. The mixture is kneaded for 5 hours, with cooling, and then introduced into 4,000 parts by volume of water. The sodium chloride and diacetone-alcohol dissolve and the pigment precipitates out. The suspension is filtered and the material on the suction filter is washed thoroughly with water and dried in a vacuum drying cabinet at 80°.

EXAMPLE 84

65 parts of stabilised polyvinyl chloride, 35 parts of dioctyl phthalate and 0.2 part of the pigment obtained according to Example 76 are stirred with one another and then worked on a twin-roll mill for 7 minutes at 140°. A red-coloured sheet with very good fastness to light and migration is obtained.

EXAMPLE 85

10 g of titanium dioxide and 2 g of the pigment prepared according to Example 76 are ground with 88 g of a mixture of 26.4 g of coconut alkyd resin, 24.0 g of melamine/formaldehyde resin (50% solids content), 8.8 g of ethylene glycol monomethyl ether and 28.8 g of xylene, for 48 hours in a ball mill.

If this surface coating is sprayed onto an aluminium foil, predried for 30 minutes at room temperature and then stoved for 30 minutes at 120° C., a red coating is obtained, which had good colour intensity and is distinguished by a very good fastness to overcoating, light and weather.

EXAMPLE 86

4 parts of the finely divided pigment according to Example 76 stirred into 20 parts of solvent of the following composition: 50 parts of Solvesso 150 (mixture of aromatic hydrocarbons), 15 parts of butyl acetate, 5 parts of Exkin II (ketoxime-based levelling agent), 25 parts of methyl isobutyl ketone and 5 parts of silicone oil (1% in Solvesso 150).

After complete fine dispersion has been reached (in about 15–60 minutes, depending on the type of stirrer), the binders are added, i.e. 48.3 parts of Baycryl L 530 (acrylic resin) (51% in xylene/butanol 3:1) and 23.7 parts of Maprenal TTX (melamine resin) (55% in butanol).

After a short period of homogenisation, the surface coating is applied by customary methods, such as spraying and dipping or, especially for the continuous coating of metal sheets, by the "coil-coating" process, and stoved (stoving: 30 minutes, 130°). The red coatings obtained are distinguished by very good levelling, high gloss and excellent fine dispersion of the pigment, and also by excellent fastness to weather.

EXAMPLE 87

If the procedure described in Example 83 is repeated, except that 2.78 parts of Staybelite Resin (HERCULES) are added to the kneading mixture, a pigment containing 10% of resin is obtained, which is distinguished by being easier to incorporate and by better dispersibility.

What is claimed is:

1. A process for the preparation of a 1:1 metal complex of an azine of the formula

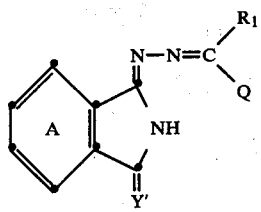

in which $R_1$ is hydrogen, alkyl or aryl, ring A is unsubstituted or is substituted by groups which do not confer solubility in water, Y' is a radical of the formula

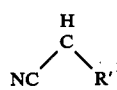

in which R' is a cyano group, an alkoxycarbonyl, alkylcarbamoyl or alkanoyl group having 2–6 C, a benzoyl, carbamoyl or sulfamoyl group, a benzylcarbamoyl or a phenylsulfamoyl or phenylsulfonyl group which is unsubstituted or substituted by halogen atoms or alkyl groups having 1–4 C, a group of the formula

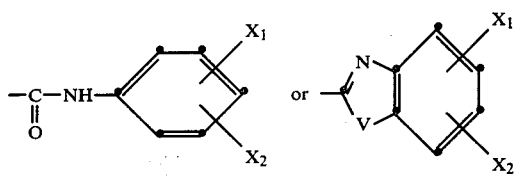

in which $X_1$ is an H, chlorine or bromine atom, a nitro, trifluoromethyl, carbamoyl or sulfamoyl group, an alkyl, alkoxy or alkylsulfamoyl group having 1–4 C, an alkanoylamino, alkylcarbamoyl or alkoxycarbonyl group having 2–6 C, or a phenoxy, benzoylamino, phenylcarbamoyl, phenylsulfamoyl or phenylazo group which is unsubstituted or substituted by chlorine or bromine atoms or methyl groups, $X_2$ is an H, chlorine or bromine atom or an alkyl or alkoxy group having 1–4 C and V is O, S or NH, Q is

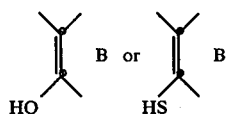

where B is a phenyl or naphthalene radical or a 5- or 6-membered heterocyclic ring which has an O, S or N atom in the α- or γ-position to the C atom on which the hydroxyl or mercapto group is located, and may also contain a further N atom in the ring or contain a fused benzene ring and/or a further heterocyclic ring, which process comprises
heating a hydrazone of the formula

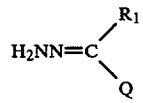

with an isoindolinone of the formula

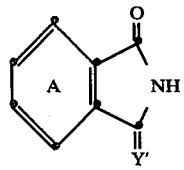  (3)

in which $R_1$, Q, A and Y' are as defined above, in the presence of a metal donor, in a polar organic solvent.

2. A process according to claim 1 where in the hydrazone $R_1$ is hydrogen or methyl, and Q is a radical containing a pyrazole, pyridine, pyrimidine, quinoline or coumarin moiety.

3. A process according to claim 1 where in the hydrazone $R_1$ is a hydrogen or methyl, and Q is a radical of the formula

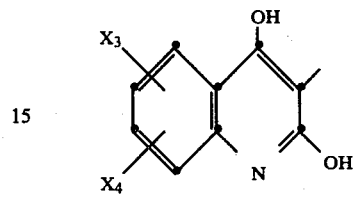

in which $X_3$ and $X_4$ independently of one another are H, Hal or alkyl having 1–4 C.

4. A process according to claim 1 where in the isoindolinone of formula (3) ring A is unsubstituted.

5. A process according to claim 1, which comprises starting from an isoindolinone of the formula (3) in which Y' is the radical of the formula

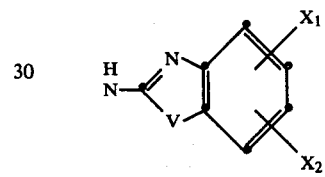

in which V, $X_1$ and $X_2$ are as defined in claim 1.

6. A process according to claim 1, which comprises using a nickel salt as the metal donor.

7. A process according to claim 1, which comprises using dimethylformamide or N-methylpyrrolidone as the polar solvent.

8. A process according to claim 1, which comprises carrying out the reaction at temperatures between 100° and 200°.

* * * * *